United States Patent
Doran Peterson et al.

(10) Patent No.: US 8,652,819 B2
(45) Date of Patent: *Feb. 18, 2014

(54) *PAENIBACILLUS* SPP. AND METHODS FOR FERMENTATION OF LIGNOCELLULOSIC MATERIALS

(75) Inventors: Joy Doran Peterson, Athens, GA (US); Emily DeCrescenzo-Henriksen, Idaho Falls, ID (US)

(73) Assignee: University of Georgia Research Foundation, Inc., Athens, GA (US)

( * ) Notice: Subject to any disclaimer, the term of this patent is extended or adjusted under 35 U.S.C. 154(b) by 245 days.

This patent is subject to a terminal disclaimer.

(21) Appl. No.: 12/993,318

(22) PCT Filed: May 22, 2009

(86) PCT No.: PCT/US2009/045067
§ 371 (c)(1),
(2), (4) Date: Mar. 8, 2011

(87) PCT Pub. No.: WO2009/143481
PCT Pub. Date: Nov. 26, 2009

(65) Prior Publication Data
US 2011/0151532 A1    Jun. 23, 2011

Related U.S. Application Data

(60) Provisional application No. 61/055,485, filed on May 23, 2008.

(51) Int. Cl.
*C12P 7/06*    (2006.01)
(52) U.S. Cl.
USPC ........................................ 435/162; 435/252.3
(58) Field of Classification Search
USPC ................................................ 435/162, 252.3
See application file for complete search history.

(56) References Cited

U.S. PATENT DOCUMENTS

| | | | |
|---|---|---|---|
| 3,844,890 | A | 10/1974 | Horikoshi et al. |
| 4,435,307 | A | 3/1984 | Barbesgaard et al. |
| 4,461,648 | A | 7/1984 | Foody |
| 4,600,590 | A | 7/1986 | Dale |
| 5,037,663 | A | 8/1991 | Dale |
| 5,972,118 | A | 10/1999 | Hester et al. |
| 7,354,743 | B2 | 4/2008 | Vlasenko et al. |
| 2005/0069998 | A1* | 3/2005 | Ballesteros Perdices et al. ............. 435/161 |
| 2007/0155000 | A1* | 7/2007 | Nilsson et al. ............ 435/161 |
| 2009/0081733 | A1 | 3/2009 | Doran-Peterson et al. |
| 2009/0093028 | A1 | 4/2009 | Doran Peterson et al. |

FOREIGN PATENT DOCUMENTS

WO    WO2009/043012 A1    4/2009

OTHER PUBLICATIONS

Barbosa et al., Appl. Environ. Microiol. Efficient fermentation of *Pinus* sp. acid hydrolysate by an ethanologenic starin of *Escherichia coli*. 58(4): 1382, 1992.*
St. John et al. Appl. Environ. Microbiol. *Paenibacillus* sp. Strain JDR-2 and XynA1: A novel system for methyglcuronxylan utilization. 72(2): 1496-1506, 2006.*
Lin et al., Ethanol fermentation from biomass resources: current state and prospects. Appl. Microbiol. Biotechnol, 69: 627-642, 2006.*
Skolnick et al., From genes to protein structure and function: novel applications of computational approaches in the genomic era. Trends in Biotech. 18: 34-39, 2000.*
Chica et al., Chica et al., Semi-rational approaches to engineering enzyme activity: combining the benefits of directed evolution and rational design. Curr. Opin. Biotechnol., 2005, vol. 16: 378-384.*
Sen et al., Developments in Directed Evolution for Improving Enzyme Functions. Appl. Biochem. Biotechnol., 2007, vol. 143: 212-223.*
Barbosa et al. "Efficient Fermentation of *Pinus* sp. Acid Hydrolysates by an Ethanologenic Strain of *Escherichia coli*". 1992. *IED and Environmental Microbiology*. 1992. 58(4):1382-1384.
Berge et al., "*Paenibacillus graminis* sp. Nov. and *Paenibacillus odorifer* sp. Nov., isolated from plant roots, soil and food" 2002. *Int J. Syst Evol MIcrobiol*, 52:607-616.
Cook et al. "Isolation of Polymer-Degrading Bacteria and the Characterization of the Hindgut Bacterial Community from the Detritus-Feeding larvae of *Tipula abdominalis* (Diptera: Tipulidae)" *Applied and Environmental Microbiology*. Sep. 2007. 73(17):5683-5686.
Camilli et al. "Insertional Mutagenesis of *Listeria monocytogenes* with a Novel Tn917 Derivative That Allows Direct Cloning of DNA Flanking Transposon Insertions" 1990. *J. Bacteriol.* 172(7):3738-3744.
Claus and Berkeley, *Bacillus*., IN Sneath, ed., 1986, *Bergey's Manual of Systematic Bacteriology*. Baltimore, The Willimas and Wilkins Co. Cover Page, Title Page, Copyright Page, Table of Contents, and pp. 1105-1139.
DeCrescenzo et al. "Polymyxin E production by *P. amylolyticus*". 2007. *Lett. Appl. Microbiol*. 45:491-496.
Doran-Peterson et al. "Microbial Conversion of Sugars from Plant Biomass to Lactic Acid or Ethanol". 2008. *The Plant Journal*. 54:582-592.
Frederick et al. "Co-production of ethanol and cellulose fiber from Southern Pine: A technical and economic assessment". 2008. *Biomass and Bioenergy*. 32:1293-1302.

(Continued)

*Primary Examiner* — Tekchand Saidha
*Assistant Examiner* — Rama P Ramanujam
(74) *Attorney, Agent, or Firm* — Mueting, Raasch & Gebhardt, P.A.

(57) ABSTRACT

Provided herein are methods for producing a fermentation product, such as ethanol, by co-culture of a member of the genus *Paenibacillus* and an ethanologenic microbe, such as yeast or *E. coli*. Also provided are methods for making enzymes useful in the saccharification of a pretreated lignocellulosic material. The enzymes may be made by culturing a member of the genus *Paenibacillus* in a composition suitable for production of such enzymes. An example of such a composition is a pretreated lignocellulosic material, for example, spent hydrolysates. Also provided are genetically modified members of the genus *Paenibacillus* that have been genetically modified to not produce an antimicrobial, for instance, a polymyxin E.

12 Claims, No Drawings

(56) References Cited

OTHER PUBLICATIONS

Galbe et al. "A Review of the Production of Ethanol from Softwood". 2002. *Appl. Microbiol. Biotechnol.* 59:618-628.
Genbank Accession No. National Center for Biotechnology Information, National Library of Medicine, National Institutes of Health, GenBank Locus AY504451, "Paenibacillaceae Bacterium C25 16S Ribosomal RNA gene, partial sequence," Retrieved on Jan. 7, 2013. Retrieved from the Internet:<URL:http://www.ncbi.nlm.nih.gov/nuccore/AY504451. 1 page.
Genbank Accession No. National Center for Biotechnology Information, National Library of Medicine, National Institutes of Health, GenBank Locus AY504452, "Paenibacillaceae Bacterium C26 16S Ribosomal RNA gene, partial sequence," Retrieved on Jan. 7, 2013. Retrieved from the Internet:<URL:http://www.ncbi.nlm.nih.gov/nuccore/AY504452. 1 page.
Genbank Accession No. National Center for Biotechnology Information, National Library of Medicine, National Institutes of Health, GenBank Locus AY504453, "Paenibacillaceae Bacterium C27 16S Ribosomal RNA gene, partial sequence," Retrieved on Jan. 7, 2013. Retrieved from the Internet:<URL:http://www.ncbi.nlm.nih.gov/nuccore/AY504453. 1 page.
Genbank Accession No. National Center for Biotechnology Information, National Library of Medicine, National Institutes of Health, GenBank Locus AY504454, "Paenibacillaceae Bacterium C28 16S Ribosomal RNA gene, partial sequence," Retrieved on Jan. 7, 2013. Retrieved from the Internet:<URL:http://www.ncbi.nlm.nih.gov/nuccore/AY504454. 1 page.
Genbank Accession No. National Center for Biotechnology Information, National Library of Medicine, National Institutes of Health, GenBank Locus AY504455, "Paenibacillaceae Bacterium C29 16S Ribosomal RNA gene, partial sequence," Retrieved on Jan. 7, 2013. Retrieved from the Internet:<URL:http://www.ncbi.nlm.nih.gov/nuccore/AY504455. 1 page.
Genbank Accession No. National Center for Biotechnology Information, National Library of Medicine, National Institutes of Health, GenBank Locus AY504456, "Paenibacillaceae Bacterium C30 16S Ribosomal RNA gene, partial sequence," Retrieved on Jan. 7, 2013. Retrieved from the Internet<URL:http://www.ncbi.nlm.nih.gov/nuccore/AY504456. 1 page.
Gong et al. "Ethanol Production from Renewable Resources" 1999. *Adv. Biochem. Engng. Biotech.* 65:207-241.
Gusakov et al. "Kinetics of the enzymatic hydrolysis of cellulose: 1. A mathematical model for a batch reactor process" 1995. *Enz. Microb. Technol.* 7:346-352.
Gusakov et al "Enhancement of Enzymatic Cellulose Hydrolysis Using a Novel Type of Bioreactor with Intensive Stirring Induced by Electromagnetic Field" 1996. *Appl. Biochem. Biotechnol.* 56:141-153.
Henriksen et al. Investigation of Lignocellulose Degrading Enzymes from *Paenibacillus amylolyticus* TA64, Isolated from the Hindgut of *Tipula abdominalis*. ASM 107th General Meeting. Toronto, Canada. Session No. 048/O. Abstract O-025. May 22, 2007. p. 493.
Heyndrickx et al., "A Polyphasic Reassessment of the Genus *Paenibacillus*, Reclassification of *Bacillus lautus* (Nakamura 1984) as *Paenibacillus lautus* comb. Nov. and of *Bacillus peoriae* (Montefusco et al. 1993) as *Paenibacillus peoriae* comb. nov., and Emended Descriptions of *P. lautus* and of *P. peoriae*" *Int J. Syst Bacteriol*, 1996; 46(4):988-1003.
International Search Report, Written Opinion issued Nov. 2, 2009, in Europe, Patent Application No. PCT/US2009/045067, filed May 22, 2009. 17 total pages.
Jeffries et al. FermentOgram. Fermentation and Biotechnology. The Division O Newsletter. The American Society for Microbiology. Spring 2007. 9 pages.
Kim et al., "*Paenibacillus pueri* sp. nov., isolated from Pu'er tea" 2009. *Int. J. Syst. Evol. Microbiol.*, 59:1002-1006.
Lynd et al. "Microbial Cellulose Utilization: Fundamentals and Biotechnology" 2002. *Microbiol. Mol. Biol. Reviews*. 66(3):506-577.

Maki et al. "The prospects of cellulase-producing bacteria for the bioconversion of lignocellulosic biomass". 2009. *Int. J. Biol. Sci.* 5(5):500-516.
Mes-Hartree et al. 1988. "Comparison of steam and ammonia pretreatment for enzymatic hydrolysis of cellulose" 1988. *Appl. Microbiol. Biotechnol*. 29:462-468.
Mondou et al. "Cloning of the xylanase gene of *Streptomyces lividans*" 1986. *Gene*. 49:323-329.
Morjanoff et al. "Optimization of Steam Explosion as a Method for Increasing Susceptibility of Sugarcane Bagasse to Enzymatic Saccharification" 1987. *Biotechnol. Bioeng*. 29:733-741.
Nakamura, "*Bacillus amylolyticus* sp. nov., nom. Rev., *Bacillus lautus* sp. nov., nom. Rev., *Bacillus pabuli* sp. nov., nom. Rev., and *Bacillus validus* sp. nov., nom. Rev." 1984. *Int J. Syst Bacteriol*, 34(2):224-226.
Neuendorf et al., "Biochemical characterization of different genotypes of *Paenibacillus larvae* subsp. larvae, a honey bee bacterial pathogen" 2004. *Microbiol.*, 150:2381-2390.
Olsson et al. "Fermentation of lignocellulosic hydrolsates for ethanol production" 1996. *Enzyme and Microb. Technol.* 18:312-331.
Pan et al. "Biorefining of Softwoods Using Ethanol Organosolv Pulping: Preliminary Evaluation of Process Streams for Manufacture of Fuel-Grade Ethanol and Co-Products" 2005. *Biotechnol. Bioeng.* 90(4):473-481.
Pan et al. "Bioconversion of Hybrid Poplar to Ethanol and CO-Products Using an Organosolv Fractionation Process: Optimization of Process Yields" 2006. *Biotechnol. Bioeng*. 94(5): 851-861.
Pan et al. "Organosolv Ethanol Lignin from Hybrid Poplar as a Radical Scavenger: Relationship between Lignin Structure, Extraction Conditions, and Antioxidant Activity" 2006. *J. Agric. Food Chem.* 54:5806-5813.
Pan et al. "Effect of Organosolv Ethanol Pretreatment Variables on Physical Characteristics of Hybrid Poplar Substrates" 2007. *Appl. Biochem. Biotechnol*. 136-140:367-377.
Pason et al. "Selection of Multienzyme Complex-Producing Bacteria Under Aerobic Cultivation". 2006. *J. Microbiol Biotechnol*. 16(8):1269-1275.
Philippidis. 1996. Cellulose bioconversion technology, in Handbook on Bioethanol: Production and Utilization, Wyman, C.E., ed., Taylor & Francis, Washington, DC 179-212.
Qian et al. "Ethanol Production from Dilute-Acid Softwood Hydrolysate by Co-Culture" 2006. *Appl. Biochem. Biotechnol*. 134:273-283.
Rastogi et al. "Isolation and characterization of cellulose-degrading bacteria from the deep subsurface of the Homestake Gold mine, Lead, South Dakota, USA". 1009.*J. Ind Microbiol Biotechnol*. 36:585-598.
Ryu et al. "Bioconversion of Waste Cellulose by Using an Attrition Bioreactor" 1983. *Biotechnol. Bioeng*. 25:53-65.
Sharrock. "Cellulase assay methods: a Review" 1988. *J. Biochem. Biophys. Methods*. 17:81-106.
Sheehan et al. 1999. Enzymes, energy and the environment: A strategic perspective on the U.S. Department of Energy's research and development activities for bioethanol, *Biotechnol. Prog*. 15(5):817-827.
Shida et al., "Emended Description of *Paenibacillus amylolyticus* and Description of *Paenibacillus illinoisensis* sp. nov. and *Paenibacillus chibensis* sp. nov." 1997. *Int J. Syst Bacteriol*, 47:299-306.
Starr et al. "Enzymatic Degradation of Polygalacturonic Acid by *Yersinia* and *Klebsiella* Species in Relation to Clinical Laboratory Procedures" 1977. *J. Clin. Microbiol*. 6(4):379-386.
St. John et al. "*Paenibacillus* sp. Strain JDR-2 and XynA1 : a Novel System for Methylglucuronoxylan Utilization" 2006. *Applied and Environmental Microbilogy*. 72(2):1496-1506.
Sun et al. "Hydrolysis of lignocellulosic materials for ethanol production: a review" 2002. *Bioresource Technol*. 83:1-11.
Tatusova et al. "BLAST 2 Sequences, a new tool for comparing protein and nucleotide sequences" *FEMS Microbiol Lett*. 1999. 174:247-250.

(56) References Cited

OTHER PUBLICATIONS

Thomas et al. "Characterization of an Extracellular β-Amylase from *Bacillus megaterium* sensu stricto" 1980. *J. Gen. Microbiol.* 118:67-72.

Waeonukul et al. "Isolation and characterization of a multienzyme complex (cellulosome) of the *Paenibacillus curdlanolytics* B-6 grown on Avicel udner aerobic conditions". 2009. *Journ. of Bioscience and Bioengineering.* 107(6):610-614.

Wang et al. "Characterization of a novel thermophilic, cellulose-degradingbacterium *Paenibacillus* sp. Strain B39" 2008. Letters in Applied Microbiology . pp. 46-53.

Wood and Kellogg. 1988. Biomass Part A: cellulose and hemicellulose. vol. 160 Academic Press, San Diego, CA. Cover Page, Title Page, Copyright Page, and Table of Contents.

Wyman et al. "Biomass Ethanol: Technical Progress, Opportunities, and Commerical Challenges" 1999. *Annu. Rev. Energy Environ.* 24:189-226.

Yoshikatsu et al., "Spoilage Ability of Psychrotrophic *Paenibacillus* spp. Isolated from Cooked Food Products" 2006. *Biocontro. Sci.*, 11(1):43-47.

DeCrescenzo-Henriksen et al. "Lignocellulosic biomass conversion to fuel ethanol: Engineering *Paenibacillus amylolyticus* TA64 for use in enzymatic pretreatment". Presentation. Published Oct. 2006. 14 pages.

\* cited by examiner

PAENIBACILLUS SPP. AND METHODS FOR FERMENTATION OF LIGNOCELLULOSIC MATERIALS

CONTINUING APPLICATION DATA

This application is the §371 U.S. National Stage of International Application No. PCT/US2009/045067, filed 22 May 2009, which claims the benefit of U.S. Provisional Application Ser. No. 61/055,485, filed May 23, 2008, each of which are incorporated by reference herein in their entireties.

BACKGROUND

The use of enzymes to saccharify lignocellulosic biomass is typically performed after other physical and/or chemical methods of pretreatment and can be accomplished prior to or in conjunction with fermentation. Pretreatment breaks down biomass to allow access to the enzymes, which can then hydrolyse the remaining cellulose, hemicellulose, and pectin polymers. Most enzymatic saccharification are performed with commercially available cell-free extracts of fungal cultures, or in some cases, bacterial cultures, designed to provide predominantly cellulase, xylanase, or pectinase hydrolysis of the lignocellulose. The fungal enzymes typically have optima of 45° C. and pH 4.5, which can differ significantly from optimal fermentation conditions, especially when the ethanologen is a bacterium.

Cellulose degradation can occur via free, secreted enzymes or by enzyme complexes attached to the surface of microorganisms (a cellulosome). While anaerobic organisms typically possess cellulosomes, aerobic bacteria and fungi typically employ free enzymes. The degradation of cellulose is achieved through the action of three types of enzymes: endoglucanases, cellobiohydrolases (or exo-glucanases), and β-glucosidases. Endo- and exo-glucanases cleave within or at the end of the glucan chain, respectively, and are classified based on both their structural fold and catalytic mechanism. Hydrolysis of cellulose by glucanases is catalyzed by two carboxyl groups in the active site and can either invert or retain configuration of the anomeric carbon. Enzymes that retain chirality use a double-displacement mechanism with a covalent enzyme-substrate intermediate while enzymes that invert chirality operate by a single-step concerted mechanism. β-glucosidases cleave cellobiose to monomeric glucose and are essential for overall cellulose degradation to glucose; accumulated cellobiose and/or glucose inhibit the activity of glucanases.

Hemicellulases are either glycoside hydrolases (GHs) or carbohydrate esterases (CEs), and are classified into families based on their activity and homology of primary sequence. GH enzymes are responsible for the hydrolysis of glycosidic bonds, while ester linked acetate and ferulic acids side chains are cleaved by CE enzymes. As the structure of hemicellulose is very heterogeneous, a wide array of enzymes is necessary for hydrolysis. Additionally, many hemicellulases have carbohydrate-binding modules in addition to catalytic domains; as much of the hemicellulose structure can be insoluble, the carbohydrate-binding modules play a role in targeting of the enzymes to the polymers.

Xylan is one major type of hemicellulose. Xylanases cleave the β-1,4 glycosidic bonds of the xylose backbone, while xylosidases hydrolyze resultant oligomers to monomeric xylose. Ferulic acid esterases and acetyl-xylan esterases cleave the ester bonds of ferulic acid and acetate side chains, respectively. Arabinofuranosidases hydrolyze arabinofuranosyl side chains from the xylose backbone and can have varying specificity as to the location of the arabinofuranosyl group. Finally, glucuronidases are responsible for the cleavage of glucuronic acid side chain α-1,2-glycosidic bonds.

A second form of hemicellulose is substituted β-mannan, such as galactomannan. Much like xylanases, β-mannanases are responsible for cleaving the mannose backbone to oligomers, which are then hydrolyzed to monomeric mannose by mannosidases. Side chain moieties, like galactose, are cleaved by respective GHs, and, in this case, by α-galactosidases.

Pectinases can be divided into three general activity groups: protopectinases, which act on insoluble pectic polymers; esterases, which de-esterify methyl and acetyl moieties from pectin; and depolymerases, which either cleave or hydrolyze glycosidic bonds with polygalacturonic acid polymers. Protopectinases are usually unnecessary for degradation of lignocellulose if physical and/or chemical pretreatment methods have been employed prior to enzymatic saccharification.

Pectin methylesterases are well described in bacteria and fungi and are responsible for the hydrolysis of the ester linkages from the polygalacturonic acid backbone. Pectin acetylesterases, which act in the same manner as pectin methylesterases to remove acetyl groups, have been described in plants and fungi; however, this type of enzyme has been found in only one bacterium, *Erwinia chrysanthemi* 3937. Pectin esterases are particularly important because many depolymerases cannot act upon methylated or acetylated pectin.

Pectin depolymerases act upon the polygalacturonate backbone and belong to one of two families: polygalacturonases or lyases. Polygalacturonases are responsible for the hydrolytic cleavage of the polygalacturonate chain, while lyases cleave by β-elimination giving a Δ4,5-unsaturated product. For pectin polymers with a rhamnogalacturonan-I backbone, other hydrolases are also necessary; rhamnosidases hydrolyze rhamnose from the backbone, and arabinofuranosidases and galactosidases cleave arabinose and galactose, respectively, from substituted rhamnose subunits.

SUMMARY OF THE INVENTION

Provided herein are methods for producing ethanol. In some aspects the methods include fermenting a composition that includes a pretreated lignocellulosic material, wherein the fermenting includes contacting the composition with an ethanologenic microbe and a *Paenibacillus* spp., such as *P. amylolyticus*. The pretreated lignocellulosic material may be present at a concentration of at least 10% solids, and the fermenting may be a simultaneous saccharification and fermentation. In some aspects the ethanologenic microbe may be a yeast, such as *Saccharomyces cerevisiae*, or a prokaryotic microbe, such as *E. coli*. The pretreated lignocellulosic material may be pine, such as *Pinus taeda*. The *Paenibacillis* spp. may produce an enzyme having saccharifying activity when incubated on a medium that includes inorganic salts and a carbon source selected from glucose, mannose, xylose, arabinose, cellulose, pectin, starch, xylan, carboxymethylcellulose, or a combination thereof.

In some aspects, the *Paenibacillis* spp. may produce an antimicrobial, such as a polymyxin, and in other aspects the *Paenibacillus* spp. is genetically modified to not produce an antimicrobial. The contacting may include inoculating the composition with the *Paenibacillis* spp. before inoculating the composition with the ethanologenic microbe, for instance, at least 12 hours before the composition is inoculated with the ethanologenic microbe. The contacting may include inoculating the composition with the *Paenibacillis* spp. and the ethanologenic microbe at substantially the same time. The method may further include adding pretreated lignocellulosic material to the composition after the fermenting has begun, for instance, at least 12 hours after the fermenting has begun.

Also provided herein are methods that include providing a composition that includes spent hydrolysates and culturing a *Paenibacillus* spp., such as *Paenibacillus amylolyticus*, in the composition under conditions suitable for the production of an enzyme having saccharifying activity. In some aspects, the *Paenibacillis* spp. may produce an antimicrobial, such as a polymyxin, and in other aspects the *Paenibacillus* spp. is genetically modified to not produce an antimicrobial. The spent hydrolysates may be obtained from fermentation of a pretreated lignocellulosic material. The *Paenibacillis* spp. may produce an enzyme having saccharifying activity when incubated on a medium that includes inorganic salts and a carbon source selected from glucose, mannose, xylose, arabinose, cellulose, pectin, starch, xylan, carboxymethylcellulose, or a combination thereof. The method may further include mixing the composition that includes the *Paenibacillis* spp. and an enzyme having saccharifying activity with a composition that includes a pretreated lignocellulosic material to result in a fermentation composition. This fermentation composition may be contacted with an enthanologenic microbe including a yeast, such as *Saccharomyces cerevisiae*, or a prokaryotic microbe, such as *E. coli*.

Further provided herein are methods including providing a first composition obtained from culturing a *Paenibacillus* spp., such as *P. amylolyticus*, in a second composition having spent hydrolysates under conditions suitable for the production of an enzyme having saccharifying activity, and mixing the first composition with a third composition that includes a pretreated lignocellulosic material to result in a fermentation composition. The fermentation composition may be contacted with an ethanologenic microbe including a yeast, such as *Saccharomyces cerevisiae*, or a prokaryotic microbe, such as *E. coli*. In some aspects, the *Paenibacillis* spp. may produce an antimicrobial, such as a polymyxin, and in other aspects the *Paenibacillus* spp. is genetically modified to not produce an antimicrobial.

Also provided herein are methods that include culturing a *Paenibacillus* spp. in a composition that includes spent hydrolysates under conditions suitable for the production of an enzyme having saccharifying activity, wherein the culturing results in a second composition that includes the *Paenibacillis* spp. and an enzyme having saccharifying activity. The *Paenibacillus* spp. may be substantially removed from the second composition. In some aspects, the *Paenibacillis* spp. may produce an antimicrobial, such as a polymyxin, and in other aspects the *Paenibacillus* spp. is genetically modified to not produce an antimicrobial.

Provided herein are genetically modified *Paenibacillus amylolyticus* that have been genetically modified to not produce an antimicrobial. The antimicrobial may be polymyxin E, and the genetically modified *P. amylolyticus* may include a transposon mutation that prevents expression of polymyxin E The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Provided herein are wild type and genetically modified *Paenibacillus* spp., and methods for using wild type and genetically modified *Paenibacillus* spp. for fermenting lignocellulosic materials into fermentation products. The term "fermentation product" means a product produced by a process including a fermentation using an ethanologenic microbe. Fermentation products contemplated according to the invention include alcohols such as, but not limited to, ethanol. Ethanol obtained according to the methods described herein may be used as fuel ethanol, drinking ethanol, e.g., potable ethanol, or industrial ethanol. A microbe described herein, for instance, a prokaryotic microbe such as a *Paenibacillus* spp. or a eukaryotic microbe such as a yeast, may be isolated. A microbe is "isolated" when it has been removed from its natural environment and can be grown as a pure culture. A genetically modified *Paenibacillus* spp. is understood to be isolated.

Members of the genus *Paenibacillus* useful in the methods disclosed herein may be obtained from soil, such as soil containing organic material, for example rice fields; food products (Yoshikatsu et al., 2006, Biocontro. Sci., 11:43-47; Kim et al., 2009, Int. J. Syst. Evol. Microbiol., 59:1002-1006), or the digestive tract of insects that have a diet that includes lignocellulosic biomass, for instance, termites, honeybee (Neuendorf et al., 2004, Microbiol., 150:2381-2390), and *Tipula abdominalis* (Cook et al., 2007, *Appl. Environ. Microbiol.*, 73:5683-5686). Whether a microbe is a member of the genus *Paenibacillus* can be determined by routine methods known to the person skilled in the art. Examples of *Paenibacillus* spp. useful in the methods described herein may include, but are not limited to, *P. amylolyticus* (Nakamura, 1984, *Int J Syst Bacteriol*, 34:224-226; Shida et al, 1997, *Int J Syst Bacteriol*, 47, 299-306), *P. pabuli* (Heyndrickx et al., 1996, *Int J Syst Bacteriol*, 46:988-1003; Nakamura, 1984, *Int J Syst Bacteriol*, 34:224-226; Shida et al, 1997, *Int J Syst Bacteriol*, 47, 299-306), *P. illinoisensis* (Berge et al., 2002, *Int J Syst Evol Microbiol*, 52:607-616; Shida et al, 1997, *Int J Syst Bacteriol*, 47, 299-306), and *P.*

*polymyxa* (Claus and Berkeley, 1986, *Bacillus*. IN Sneath, ed., *Bergey's Manual of Systematic Bacteriology*. Baltimore, The Willimas and Wilkins Co.; Heyndrickx et al., 1996, *Int J Syst Bacteriol*, 46:988-1003). When the *Paenibacillus* is *P. amylolyticus*, the *P. amylolyticus* may include a 16S rRNA sequence that is similar to, or identical to a 16S rRNA nucleotide sequence available at the Genbank database under accession numbers AY504451, AY504452, AY504453, AY504454, AY504455, or AY504456. Determining the nucleotide sequence of a 16S rRNA coding sequence can be accomplished using routine methods known to the person skilled in the art.

The similarity between a 16S rRNA sequence present in a *P. amylolyticus* and a 16S rRNA nucleotide sequence available at the Genbank database under accession numbers AY504451, AY504452, AY504453, AY504454, AY504455, or AY504456 is referred to as structural similarity and is determined by aligning the residues of the two sequences (i.e., the nucleotide sequence of a 16S rRNA sequence present in a *P. amylolyticus* and the sequence present at AY504451, AY504452, AY504453, AY504454, AY504455, or AY504456) to optimize the number of identical nucleotides along the lengths of their sequences; gaps in either or both sequences are permitted in making the alignment in order to optimize the number of shared nucleotides, although the nucleotides in each sequence must nonetheless remain in their proper order. Two nucleotide sequences may be compared using the BESTFIT algorithm in the GCG package (version 10.2, Madison Wis.), or the Blastn program of the BLAST 2 search algorithm, as described by Tatusova, et al. (FEMS Microbiol Lett 1999, 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, structural similarity is referred to as "identities." Preferably, a *P. amylolyticus* 16S rRNA includes a nucleotide sequence having a structural similarity with the sequence present at AY504451, AY504452, AY504453, AY504454, AY504455, or AY504456 of at least 95%, at least 96%, at least 97%, at least 98%, or at least 99% identity.

A member of the genus *Paenibacillus* typically has characteristics that include: ability to grow under anaerobic conditions; catalase activity; ability to produce acid from arabinose, glucose, mannitol, and/or xylose; starch hydrolysis activity; ability to grow in 2% NaCl; and ability to grow at pH 5.6. Optionally, a member of the genus *Paenibacillus* may have characteristics including nitrate reduction activity, caesin hydrolysis activity, and ability to grow in 0.001% lysozyme.

A member of the genus *Paenibacillus* useful in the methods described herein has the characteristic of producing enzymes having saccharifying activity. The enzyme having saccharifying activity may be secreted. As used herein, saccharifying refers to breaking a complex carbohydrate (as starch or cellulose) into disaccharide components, such as cellobiose, and monosaccharide components, such as glucose. Examples of such activities include, but are not limited to, xylanase activity, pectinase activity, amylase activity, mannanase activity, and cellulase (such as carboxymethylcellulase) activity. Examples of cellulase activity include endo-acting and exo-acting cellulases. A member of the genus *Paenibacillus* useful in the methods described herein may produce one or more enzymes having saccharifying activity during growth in aerobic conditions, microaerophilic conditions, and/or anaerobic conditions.

Whether a member of the genus *Paenibacillus* produces an enzyme having one of these activities may be determined using routine methods known to the person skilled in the art. For example, a member of the genus *Paenibacillus* may be grown in a defined basal medium that includes 7 grams $K_2HPO_4$/liter, 3 grams $KH_2PO_4$/liter, 1 grams $(NH_4)_2SO_4$/liter, 0.5 grams sodium citrate/liter, and 0.1 grams $MgSO_4$-$7H_2O$/liter. The defined basal medium may be supplemented with different carbohydrates, individually or in combination, at 1% (wt/vol), and after growth in the medium for 48 hours the supernatant can be collected via centrifugation and assayed for the presence of, for instance, xylanase, pectinase, amylase, and cellulase activity using routine methods known to the person skilled in the art. For instance, methods for assaying enzymatic activities on the following model substrates are routine and well known: carboxymethylcellulose (Wood and Kellogg, 1988, Biomass part A: cellulose and hemicellulose, vol. 160. Academic Press, San Diego, Calif.); starch (Thomas et al., 1980, J. Gen. Microbiol., 118:67-72); xylan (Mondou et al., 1986, Gene, 49:323-330); polygalacturonate (Starr et al., 1977, J. Clin. Microbiol., 6:379-386); and methylumbelliferyl conjugates of cellobiopyranoside, arabinofuranoside, glucoside, mannopyranoside, and xyloside (Sharrock, 1988, J. Biochem. Biophys. Methods 17:81-106). Examples of carbohydrates that can be added to the defined basal medium include, but are not limited to, glucose, mannose, xylose, arabinose, cellulose, pectin (for instance, polygalacturonate), starch, xylan, and carboxymethylcellulose. Complex mixtures of carbohydrates may also be added, such as pretreated lignocellulosic material derived from, for instance, pine or Bermudagrass. Pretreated lignocellulosic material is described herein. After growth on the defined basal medium supplemented with a carbohydrate at 1% (wt/vol) for 48 hours, a member of the genus *Paenibacillus* useful in the methods described herein may produce an enzyme having saccharifying activity, such as a xylanase, a pectinase, an amylase, and/or a cellulase at a concentration of at least 0.1, at least 0.15, at least 0.2, at least 0.25, at least 0.3, at least 0.35, at least 0.4, or at least 0.45 International Units per milliliter (IU/ml).

A member of the genus *Paenibacillus*, such as *P. amylolyticus*, may have the characteristic of producing phenolic acid decarboxylases, for example, enzymes converting phenolic acids to aromatic 4-vinyl derivatives, with no need for additional cofactors. Examples of such phenolic acids include, for instance, ferulic, p-coumaric, and/or caffeic acids. These are expected to aid in detoxifing hydroxycinnamic acids released after plant cell wall degradation.

Examples of *P. amylolyticus* strains useful in the methods disclosed herein include, but are not limited to, 27C64, C26, C27, C28, C29, and C30 (Cook et al., 2007, *Appl. Environ. Microbiol.*, 73:5683-5686; Doran-Peterson and Decrescenzo-Henriksen, U.S. Patent Application 20090081733).

Optionally, a member of the genus *Paenibacillus* useful in the methods described herein expresses an antimicrobial. An antimicrobial is a compound that is able to inhibit growth (e.g., replication) or kill a microbe. Preferably, an antimicrobial inhibits or kills a Gram negative microbe, a Gram positive microbe, or both Gram negative and Gram positive microbes. Preferably, an antimicrobial produced by a member of the genus *Paenibacillus* useful in the methods described herein does not inhibit or kill a eukaryotic microbe.

The production of an antimicrobial by a member of the genus *Paenibacillus* can be determined by routine screening methods. For instance, a candidate *Paenibacillus* can be incubated under conditions suitable for replication, such as aerobic or anaerobic conditions, and other microbial isolates (referred to as indicator strains) can be exposed to the candidate *Paenibacillus*. A candidate *Paenibacillus* is the isolate being assayed for the production of an antimicrobial. Indicator strains may be either Gram negative (such as, but not limited to, *E. coli* and *Salmonella* spp.) or Gram positive (such as, but not limited to, *Staphylococcus aureus* and *Bacillus subtilis*). Methods for using indicator strains to evaluate the activity of an antimicrobial are routine and known to the skilled person. For instance, indicator strains can be exposed to a culture supernatant obtained from medium in which the candidate *Paenibacillus* was grown, or the indicator strains can be grown on the same solid medium as the candidate *Paenibacillus* in such a way to result in overlapping growth of the candidate *Paenibacillus* and the indicator strains. The inhibition of growth of an indicator strain is evidence the *Paenibacillus* produces an antimicrobial.

An example of an antimicrobial that may be produced by a member of the genus *Paenibacillus* useful in the methods described herein is a polymyxin, such as polymyxin E1 (also known as colistin A) or polymyxin E2 (also known as colistin B). A *Paenibacillus* may produce both. For instance, a polymyxin produced by a *P. amylolyticus* may include leucine and threonine, and either lysine, 2,4-diaminobutyric acid, or a combination thereof. The molecular weight of a polymyxin produced by a *P. amylolyticus* may be 1,155 or 1,169 Daltons (see Doran-Peterson and Decrescenzo-Henriksen, U.S. Patent Application 20090081733).

In some aspects, a member of the genus *Paenibacillus* useful in the methods described herein does not express an antimicrobial. Such strains can be obtained by routine screening for antimicrobial-deficient members of the genus *Paenibacillus*. Alternatively, a member of the genus *Paenibacillus* useful in the methods described herein that produces an antimicrobial can be modified to result in a genetically modified *Paenibacillus* that does not produce an antimicrobial. As used herein, "genetically modified" microbe refers to a microbe that has been altered "by the hand of man." For example, a microbe is a genetically modified microbe by virtue of introduction into a suitable microbe of an exogenous polynucleotide. "Genetically modified microbe" also refers to a microbe that has been genetically manipulated such that endogenous nucleotides have been altered. For example, a microbe is a genetically modified microbe by virtue of introduction into a suitable microbe of an alteration of endogenous nucleotides. For instance, an endogenous coding region could be deleted or mutagenized. Such mutations may result in a polypeptide having a different amino acid sequence than was encoded by the endogenous polynucleotide.

Methods for genetically modifying *Paenibacillus* spp. include those useful for genetically modifying members of the genus *Bacillus*, such as *B. subtilus*. Such methods are routine and known to the person skilled in the art. Methods that may be used to result in a genetically modified *Paenibacillus* that does not produce an antimicrobial include random mutagenesis methods, such as transposon mutagenesis or exposure of cells to a mutagen, such as nitrosoguanidine. For instance, a *Paenibacillus* spp. may be subjected to mutagenesis by introducing a transposon into *Paenibacillus* spp. cells, and screening the resulting cells to identify colonies that do not produce the antimicrobial.

Provided herein are methods for fermenting lignocellulosic material into fermentation products. The process of producing fermentation products, preferably ethanol, from lignocellulosic materials typically includes pretreatment, enzymatic hydrolysis through the use of cellulases, fermentation, and recovery of the fermentation product. The process may also include, for instance, separation of the sugar solution from residual materials such as lignin. The methods disclosed herein typically include using saccharifying enzymes produced by a wild type or genetically modified *Paenibacillus* spp.

Any suitable lignocellulosic material is contemplated in context of the present methods. Lignocellulosic material may be any material containing lignocellulose. In some aspects, the lignocellulosic material contains at least 50 wt %, preferably at least 70 wt %, more preferably at least 90 wt % lignocellulose. It is to be understood that the lignocellulosic material may also include other constituents such as cellulosic material, such as cellulose, hemicellulose, and may also include constituents such as sugars, such as fermentable sugars and/or un-fermentable sugars.

Lignocellulosic material is generally found, for example, in the stems, leaves, hulls, husks, and cobs of plants or leaves, branches, and wood of trees. Lignocellulosic material can also be, but is not limited to, herbaceous material, agricultural residues, forestry residues, municipal solid wastes, waste paper, and pulp and paper mill residues. It is understood herein that lignocellulose material may be in the form of plant cell wall material containing lignin, cellulose, and hemicellulose in a mixed matrix. In some aspects the lignocellulosic material is corn fiber, rice straw, pine wood such as *Pinus taeda*, poplar, wheat straw, switchgrass, Bermudagrass, paper and pulp processing waste, corn stover, corn fiber, hardwood such as poplar and birch, softwood such as Doulas fir and pine and spruce, cereal straw such as wheat straw, municipal solid waste, industrial organic waste, office paper, sugarcane and bagasse, sugarbeets and pulp, sweet potatoes with skins, food processing wastes or mixtures thereof.

The steps following pretreatment, e.g., hydrolysis and fermentation, can be performed separately or simultaneously. Conventional methods used to process the lignocellulosic material in accordance with the methods disclosed herein are well understood to those skilled in the art. Detailed discussion of methods and protocols for the production of ethanol from biomass are reviewed in Wyman (1999, Annu. Rev. Energy Environ., 24:189-226), Gong et al. (1999, Adv. Biochem. Engng. Biotech., 65: 207-241), Sun and Cheng (2002, Bioresource Technol., 83:1-11), and Olsson and Hahn-Hagerdal (1996, Enzyme and Microb. Technol., 18:312-331). The methods of the present invention may be implemented using any conventional biomass processing apparatus (also referred to herein as a bioreactor) configured to operate in accordance with the invention. Such an apparatus may include a batch-stirred reactor, a continuous flow stirred reactor with ultrafiltration, a continuous plug-flow column reactor (Gusakov, A. V., and Sinitsyn, A. P., 1985, Enz. Microb. Technol., 7: 346-352), an attrition reactor (Ryu, S. K., and Lee, J. M., 1983, Biotechnol. Bioeng., 25: 53-65), or a reactor with intensive stirring induced by an electromagnetic field (Gusakov, A. V., Sinitsyn, A. P., Davydkin, I. Y., Davydkin, V. Y., Protas, O. V., 1996, Appl. Biochem. Biotechnol., 56: 141-153). Smaller scale fermentations may be conducted using, for instance, a flask or a fleaker.

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC). The fermentation can be carried out by batch fermentation or by fed-batch fermentation.

SHF uses separate process steps to first enzymatically hydrolyze cellulose to glucose and then ferment glucose to ethanol. In SSF, the enzymatic hydrolysis of cellulose and the fermentation of glucose to ethanol are combined in one step (Philippidis, G. P., 1996, Cellulose bioconversion technology, in Handbook on Bioethanol: Production and Utilization, Wyman, C. E., ed., Taylor & Francis, Washington, D.C., 179-212). SSCF includes the coferementation of multiple sugars (Sheehan, J., and Himmel, M., 1999, Enzymes, energy and the environment: A strategic perspective on the U.S. Department of Energy's research and development activities for bioethanol, Biotechnol. Prog., 15: 817-827). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbiol. Mol. Biol. Reviews, 66: 506-577).

There are numerous pretreatment methods or combinations of pretreatment methods known in the art and routinely used. Physical pretreatment breaks down the size of lignocellulosic material by milling or aqueous/steam processing. Chipping or grinding may be used to typically produce particles between 0.2 and 30 mm in size. Methods used for lignocellulosic materials typically require intense physical pretreatments such as steam explosion and other such treatments (Peterson et al., U.S. Patent Application 20090093028). The most common chemical pretreatment methods used for lignocellulosic materials include dilute acid, alkaline, organic solvent, ammonia, sulfur dioxide, carbon dioxide or other chemicals to make the biomass more available to enzymes. Biological pretreatments are sometimes used in combination with chemical treatments to solubilize the lignin in order to make cellulose more accessible to hydrolysis and fermentation.

Steam explosion is a common method for pretreatment of lignocellulosic biomass and increases the amount of cellulose available for enzymatic hydrolysis (Foody, U.S. Pat. No. 4,461,648). Generally, the material is treated with high-pressure saturated steam and the pressure is rapidly reduced, causing the materials to undergo an explosive decompression. Steam explosion is typically initiated at a temperature of 160-260° C. for several seconds to several minutes at pressures of up to 4.5 to 5 MPa. The biomass is then exposed to atmospheric pressure. The process typically causes hemicellulose degradation and lignin transformation. Addition of $H_2SO_4$, $SO_2$, or $CO_2$ to the steam explosion reaction can improve subsequent cellulose hydrolysis, decrease production of inhibitory compounds and lead to the more complete removal of hemicellulose (Morjanoff and Gray, 1987, Biotechnol. Bioeng. 29:733-741).

In ammonia fiber explosion (AFEX) pretreatment, biomass is treated with approximately 1-2 kg ammonia per kg dry biomass for approximately 30 minutes at pressures of 1.5 to 2 MPa. (Dale, U.S. Pat. No. 4,600,590; Dale, U.S. Pat. No. 5,037,663; Mes-Hartree, et al. 1988, Appl. Microbiol. Biotechnol., 29:462-468). Like steam explosion, the pressure is then rapidly reduced to atmospheric levels, boiling the ammonia and exploding the lignocellulosic material. AFEX pretreatment appears to be especially effective for biomass with a relatively low lignin content, but not for biomass with high lignin content such as newspaper or aspen chips (Sun and Cheng, 2002, Bioresource Technol., 83:1-11).

Concentrated or dilute acids may also be used for pretreatment of lignocellulosic biomass. $H_2SO_4$ and HCl have been used at high concentrations, for instance, greater than 70%. In addition to pretreatment, concentrated acid may also be used for hydrolysis of cellulose (Hester et al., U.S. Pat. No. 5,972, 118). Dilute acids can be used at either high (>160° C.) or low (<160° C.) temperatures, although high temperature is preferred for cellulose hydrolysis (Sun and Cheng, 2002, Bioresource Technol., 83:1-11). $H_2SO_4$ and HCl at concentrations of 0.3 to 2% (wt/wt) and treatment times ranging from minutes to 2 hours or longer can be used for dilute acid pretreatment.

Other pretreatments include alkaline hydrolysis (Qian et al., 2006, Appl. Biochem. Biotechnol., 134:273; Galbe and Zacchi, 2002, Appl. Microbiol. Biotechnol., 59:618), oxidative delignification, organosolv process (Pan et al., 2005, Biotechnol. Bioeng., 90:473; Pan et al., 2006, Biotechnol. Bioeng., 94:851; Pan et al., 2006, J. Agric. Food Chem., 54:5806; Pan et al., 2007, Appl. Biochem. Biotechnol., 137-140:367), or biological pretreatment.

Some of the pretreatment processes described above include hydrolysis of the hemicellulose and cellulose to monomer sugars. Others, such as organosolv, prepare the substrates so that they will be susceptible to hydrolysis. This hydrolysis step can in fact be part of the fermentation process if some methods, such as simultaneous saccharification and fermentation (SSF), is used. Otherwise, the pretreatment may be followed by enzymatic hydrolysis with cellulases.

A cellulase may be any enzyme involved in the degradation of lignocellulose to glucose, xylose, mannose, galactose, and arabinose. The cellulolytic enzyme may be a multicomponent enzyme preparation, e.g., cellulase, a monocomponent enzyme preparation, e.g., endoglucanase, cellobiohydrolase, glucohydrolase, beta-glucosidase, or a combination of multicomponent and monocomponent enzymes. The cellulolytic enzymes may have activity, e.g., hydrolyze cellulose, either in the acid, neutral, or alkaline pH-range.

A cellulase may be of fungal or bacterial origin, which may be obtainable or isolated from microorganisms which are known to be capable of producing cellulolytic enzymes, e.g., species of *Humicola, Coprinus, Thielavia, Fusarium, Myceliophthora, Acremonium, Cephalosporium, Scytalidium, Penicillium* or *Aspergillus* (see, for example, EP 458162), especially those produced by a strain selected from the species *Humicola insolens* (reclassified as *Scytalidium thermophilum*, see for example, Barbesgaard et al., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Trichoderma* (particularly *Trichoderma*

*viride, Trichoderma reesei*, and *Trichoderma koningii*), alkalophilic *Bacillus* (see, for example, Horikoshi et al., U.S. Pat. No. 3,844,890 and EP 458162), and *Streptomyces* (see, for example, EP 458162). Useful cellulases may be produced by fermentation of the above-noted microbial strains on a nutrient medium containing suitable carbon and nitrogen sources and inorganic salts, using procedures known in the art.

Examples of cellulases suitable for use in the present invention include, for example, CELLUCLAST (available from Novozymes A/S) and NOVOZYME (available from Novozymes A/S). Other commercially available preparations including cellulase which may be used include CEL-LUZYME, CEREFLO and ULTRAFLO (Novozymes A/S), LAMINEX and SPEZYME CP (Genencor Int.), and ROHA-MENT 7069 W (Rohm GmbH).

Typically, cellulase enzymes may be added in amounts effective from 5 to 35 filter paper units (FPU) of activity per gram of substrate, or 0.001% to 5.0% wt. of solids. In those aspects of the methods described herein where the hydrolysis and fermentation following pretreatment are performed separately (e.g., SHF), the cellulase enzymes typically used for hydrolysis may be supplemented with enzymes produced by a *Paenibacillus* spp. described herein. *Paenibacillus* spp. derived enzymes may be obtained by growing a *Paenibacillus* spp. under conditions suitable for the production of enzymes having saccharifying activity. Conditions that are "suitable" for an event to occur, such as production of enzymes having saccharifying activity, or "suitable" conditions are conditions that do not prevent such events from occurring. Thus, these conditions permit, enhance, facilitate, and/or are conducive to the event. Suitable conditions include growth in a medium that includes pretreated lignocellulosic material. An example of a pretreated lignocellulosic material includes spent hydrolysates, e.g., the material remaining after lignocellulosic material is subjected to pretreatment, hydrolysis, fermentation, and recovery of a fermentation product. Typically, the spent hydrolysate includes a carbon source, e.g., carbohydrates, that were not catabolized by an ethanologenic microbe during a fermentation. In one aspect, when the ethanologenic microbe is a yeast that does not use pentoses, such as xylose, the pentoses present in the spent hydrolysate can be used by a *Paenibacillus* spp. as a carbon source. Spent hydrolysates may be supplemented with nutrients such as, but not limited to, components of the defined basal medium described herein to promote growth of a *Paenibacillus* spp. In some aspects, a spent hydrolysate is not supplemented with a carbon source, and in other aspects, for instance when production of the spent hydrolysate consumes all carbon sources, the spent hydrolysate may be supplemented with a carbon source. Conditions suitable for growth of a *Paenibacillus* spp. in spent hydrolysates include between 25° C. and 37° C., and pH of between 5 and 7. The production of enzymes by *Paenibacillus* spp. during the growth in the spent hydrolysates may be monitored using routine methods known to the skilled person.

The spent hydrolysate containing *Paenibacillus* spp. and enzymes produced during the incubation can be used for saccharification of lignocellulosic materials before fermentation. For instance, if the incubation of a *Paenibacillus* spp. in spent hydrolysate was in a bioreactor, pretreated lignocellulosic material may be added and hydrolysis allowed to proceed. Alternatively, the spent hydrolysate, now containing enzymes produced by the *Paenibacillus* spp., can be transferred to a bioreactor. Optionally, the *Paenibacillus* spp. may be substantially removed by, for instance, centrifugation prior to the transfer. The hydrolysis of the pretreated lignocellulosic material may, and typically does, require addition of cellulases often used in the hydrolysis of lignocellulosic material; however, the amount of cellulases (e.g., cellulases available from Novozymes A/S) appropriate for the hydrolysis is decreased due to the presence of the enzymes produced by the *Paenibacillus* spp. Typically, the amount of cellulases (e.g., cellulases available from Novozymes A/S) required for hydrolysis of the pretreated lignocellulosic material is decreased by at least 5%, at least 10%, at least 15%, at least 20%, at least 25%, or at least 30%. Thus, cellulase enzymes typically added at 5 to 35 FPU of activity per gram of substrate can be decreased, for instance, to between 4.5 and 31.5 FPU of activity per gram of substrate, or to between 4.5 and 28 FPU of activity per gram of substrate. Furthermore, in this and other aspects, the ethanol in a fermentation is produced in a shorter period of time. This decreased need for cellulases can result in a significant decrease in costs associated with producing fermentation products from lignocellulosic materials. A *Paenibacillus* spp. may be prepared for addition to pretreated lignocellulosic materials, e.g., spent hydrolysates, by routine culturing of *Paenibacillus* spp. For instance, a *Paenibacillus* spp. may be incubated in liquid medium, concentrated by centrifugation, and suspended in medium at a concentration that permits addition of a suitable volume to result in an appropriate number of cells added to the spent hydrolysates. Typically, enough cells are added to result in at least $5 \times 10^4$, at least $1 \times 10^5$, or at least $5 \times 10^5$ cells per milliliter of spent hydrolysate. Optionally, the culture broth is also added to the spent hydrolysate. For instance, the supernatant resulting from concentrating the cells is added. Reaction conditions for enzymatic hydrolysis using cellulases and enzymes produced by a *Paenibacillus* spp. are typically pH 5 to 7 at a temperature between 30° C. and 37° C. with incubations of between 12 and 24 hours. Surfactants may also be used during enzyme hydrolysis to improve cellulose conversion (Vlasenko et al., U.S. Pat. No. 7,354,743). In those aspects wherein the culture broth is added, the mixture of culture broth and pretreated lignocellulosic material, such as spent hydrolysates, may be incubated at an elevated temperature before addition of an ethanologenic microbe, such as a temperature between 40° C. and 60° C., or between 45° C. and 55° C. Typically, if the enzymes are to be used with lignocellulosic materials that will be fermented with a prokaryotic microbe, such as *E. coli*, the *Paenibacillus* spp. is typically one that does not produce an antimicrobial that is active against Gram negative microbes. If the enzymes are to be used with lignocellulosic materials that will be fermented with a eukaryotic microbe, such as yeast, the *Paenibacillus* spp. is typically one that does produce an antimicrobial that is active against prokaryotic microbes. It is expected that other microbes, including *Clostridium* spp. such as *C. thermocellum, C. phytofermentans, Byssovorax cruenta, Eubacterium cellulosolvens*, and *Cellvibrio mixtus* may also be used to produce saccharifying enzymes by growth on spent hydrolysates, and those enzymes may be used to supplement hydrolysis of pretreated lignocellulosic materials.

In those aspects of the methods described herein where the hydrolysis and fermentation steps following pretreatment are performed simultaneously (e.g., SSF), the cellulase enzymes typically used for hydrolysis (e.g., cellulases available from Novozymes A/S) may be supplemented by co-culturing an ethanologenic microbe with a *Paenibacillus* spp. described herein during the hydrolysis/fermentation. Co-culture may also be used during the fermentation step of a process that includes separate hydrolysis and fermentation steps. *Paenibacillus* spp. may be added to pretreated lignocellulosic material prior to addition of an ethanologenic microbe, or added to pretreated lignocellulosic material at the same time an ethanologenic microbe is added. Addition of a *Paenibacilus* spp. to a fermentation was expected to result in decreased ethanol production since an ethanologenic microbe and a *Paenibacilus* spp. would compete for the same carbon source; however, there was found to be no decrease in ethanol production, and in some aspects, maximum ethanol production occurs in less time.

A *Paenibacillus* spp. may be prepared for addition to pretreated lignocellulosic materials by routine culturing of *Paenibacillus* spp. For instance, a *Paenibacillus* spp. may be incubated in liquid medium, concentrated by centrifugation, and suspended in medium at a concentration that permits addition of a suitable volume to the hydrolysate/fermentation volume to result in an appropriate number of cells per milliliter. Typically, enough cells are added to result in at least $5\times10^4$, at least $1\times10^5$, or at least $5\times10^5$ cells per milliliter of hydrolysis/fermentation volume. Optionally, the culture broth resulting from growth of a *Paenibacillus* spp. is also added to the hydrolysis/fermentation volume. For instance, the supernatant resulting from concentrating the cells is added. The culture broth may be at least 10%, at least 20%, at least 30%, or at least 40% of the total volume of the hydrolysis/fermentation mixture.

The hydrolysis/fermentation of the pretreated lignocellulosic material may, and typically does, require addition of cellulases (e.g., cellulases available from Novozymes A/S); however, the amount of cellulases appropriate for the hydrolysis is decreased due to the presence of the enzymes produced by the *Paenibacillus* spp. Typically, the amount of cellulases (e.g., cellulases available from Novozymes A/S) required for hydrolysis of the pretreated lignocellulosic material is decreased by at least 5%, at least 10%, at least 15%, at least 20%, at least 25%, or at least 30%. This decreased need for cellulases can result in a significant decrease in costs associated with producing fermentation products from lignocellulosic materials. Conditions suitable for simultaneous hydrolysis and fermentation are typically pH 5 to 7 at a temperature between 30° C. and 37° C. with incubations of between 24 and 96 hours or longer, such as continuous fermentations. Typically, if the ethanologenic microbe is a prokaryotic microbe, such as *E. coli*, the *Paenibacillus* spp. is typically one that does not produce an antimicrobial that is active against prokaryotic microbes. If the ethanologenic microbe is a eukaryotic microbe, such as yeast, the *Paenibacillus* spp. is typically one that does produce an antimicrobial that is active against prokaryotic microbes. It is expected that other microbes, including *Cellulomonas* spp., such as *C. fimi*, may also be used in co-culture with an ethanologenic microbe produce saccharifying enzymes during a hydrolysis/fermentation.

Ethanol fermentation is the biological process by which sugars such as glucose are converted into cellular energy, thereby producing ethanol and carbon dioxide as metabolic waste products. Ethanologenic microbes typically carry out ethanol fermentation on sugars in the absence of oxygen. Since the process does not require oxygen, ethanol fermentation is classified as anaerobic. In general, the process begins with a molecule of glucose being broken down by the process of glycolysis into pyruvate. This reaction is accompanied by the reduction of two molecules of $NAD^+$ to NADH and a net of two ADP molecules converted to two ATP plus the two water molecules. Pyruvate is then converted to acetaldehyde and carbon dioxide. The acetaldehyde is subsequently reduced to ethanol by the NADH from the previous glycolysis, which is returned to $NAD^+$. For maximum efficiencies, both pentose sugars from the hemicellulose fraction of the lignocellulosic material (e.g. xylose) and hexose sugars from the cellulose fraction (e.g. glucose) can be used.

A fermentation is typically begun by adding an ethanologenic microbe to a fermentation mixture of pretreated lignocellulosic material, or in some aspects, hydrolyzed pretreated lignocellulosic material. Optionally, a *Paenibacillus* spp. may be added to a fermentation mixture prior to, or at the same time as, the ethanologenic microbe. The amount of solids present at the beginning of a fermentation may be from 8% to 17% weight of solids per volume of fermentation mixture (wt/vol), from 10% to 15% wt/vol, or 12% wt/vol. As used herein, "solids" refers to total dry weight of a pretreated lignocellulosic material. The ethanologenic microbe may be added to the fermentation medium so that the viable ethanologenic microbe, such as yeast, is present in the fermentation medium in a range from $10^5$ to $10^{12}$, such as from $10^7$ to $10^{10}$ cells per milliliter. Fermentation with ethanologenic microbes, e.g., yeast strains, is typically optimal around temperatures of 26° C. to 40° C., such as 30° C. to 37° C. A fermentation may be carried out for between 25 and 190 hours, 40 to 170 hours, or 60 to 150 hours.

Optionally, during a fermentation the fermentation mixture may be supplemented with additional solids. For instance, between 2% and 5% wt/vol solids may be added at intervals of, for example, 12 hours or 24 hours. In one aspect, a fermentation may be supplemented with solids at 12 hours, 24 hours, and 36 hours. Optionally, during a fermentation the fermentation mixture may be supplemented with additional amounts of an ethanologenic microbe. For instance, $1\times10^6$, $1\times10^7$, or $1\times10^8$ cells per milliliter of an ethanologenic microbe may be added at intervals of, for example, 12 hours or 24 hours.

The term "ethanologenic microbe" refers to any organism, including prokaryotic and eukaryotic microbes, such as yeast and filamentous fungi, suitable for producing a desired fermentation product. Especially suitable ethanologenic microbes useful in the methods disclosed herein are able to ferment, i.e., convert sugars, such as glucose, fructose maltose, xylose, mannose and/or arabinose, directly or indirectly into the desired fermentation product. Examples of eukaryotic ethanologenic microbes include fungal organisms, such as yeast. Preferred yeast includes strains of the genus *Saccharomyces*, in particular *Saccharomyces cerevisiae* or *Saccharomyces uvarum*; members of the genus *Pichia*, in particular *Pichia stipitis* or *Pichia pastoris*; members of the genus *Candida*, in particular *Candida utilis, Candida arabinofermentans, Candida diddensii, Candida sonorensis, Candida shehatae, Candida tropicalis*, or *Candida boidinii*. Other contemplated yeast includes members of the genus *Hansenula*, in particular *Hansenula polymorpha* or *Hansenula anomala*; members of the genus *Kluyveromyces*, in particular *Kluyveromyces marxianus* or *Kluyveromyces fagilis*, and members of the genus *Schizosaccharomyces*, in particular *Schizosaccharomyces pombe*.

Examples of commercially available suitable yeast include, e.g., RED STAR and ETHANOL RED yeast (available from Fermentis/Lesaffre, USA), FALI (available from Fleischmann's Yeast, USA), SUPERSTART and THERMOSACC fresh yeast (available from Ethanol Technology, Wis., USA), BIOFERM AFT and XR (available from NABC—North American Bioproducts Corporation, GA, USA), GERT STRAND (available from Gert Strand AB, Sweden), and FERMIOL (available from DSM Specialties). Genetically modified yeast may be used in certain aspects of the methods described herein, including those capable of converting hexoses and pentoses to ethanol.

Examples of prokaryotic ethanologenic microbes include, but are not limited to, *Escherichia*, in particular *Escherichia coli*, members of the genus *Zymomonas*, in particular *Zymomonas mobilis*, members of the genus *Zymobacter*, in particular *Zymobactor palmae*, members of the genus *Klebsiella*, in particular *Klebsiella oxytoca*, members of the genus *Leuconostoc*, in particular *Leuconostoc mesenteroides*, members of the genus *Clostridium*, in particular *Clostridium butyricum*, members of the genus *Enterobacter*, in particular *Enterobacter aerogenes*, and members of the genus *Thermoanaerobacter*, in particular *Thermoanaerobacter* BG1L1 (Appl. Microbiol. Biotech. 77: 61-86) and *Thermoanarobacter ethanolicus*, *Thermoanaerobacter thermosaccharolyticum*, or *Thermoanaerobacter mathranii*. Members of the genus *Lactobacillus* are also envisioned as are strains of *Corynebacterium glutamicum* R, *Bacillus thermoglucosidaisus*, and *Geobacillus thermoglucosidasius*.

The final step may be recovery of the fermentation product. The fermentation product may be distilled using conventional methods producing ethanol, for instance 95% ethanol. For example, after fermentation the fermentation product, e.g., ethanol, may be separated from the fermented slurry. The slurry may be distilled to extract the ethanol, or the ethanol may be extracted from the fermented slurry by micro or membrane filtration techniques. Alternatively the fermentation product may be recovered by stripping. Methods for recovery are known in the art and used routinely. The material remaining after recovery of the fermentation product is spent hydrolysate.

The present invention is illustrated by the following examples. It is to be understood that the particular examples, materials, amounts, and procedures are to be interpreted broadly in accordance with the scope and spirit of the invention as set forth herein.

EXAMPLE 1

Use of enzymes produced by *Paenibacillus amylolyticus*, including, but not limited to saccharifying enzymes, to breakdown substrates composed of cellulose, hemicellulose, lignin, and/or pectin.

*P. amylolyticus* isolate C27, referred to herein as *P. amylolyticus* C27, was isolated from a hindgut extract of a *Tipula abdominalis* larva (Cook et al., Appl. Environ. Microbiol., 2007, 73:5683-5686; DeCrescenzo Henriksen et al., Lett. Appl. Microbiol., 2007, 45:491-496). *P. amylolyticus* C27 was grown on basal minimal media with 1% (wt/vol) carbon sources as listed in the Table 1. After 48 hours, supernatant was collected via centrifugation and assayed for xylanase, pectinase, amylase, and CMCase (cellulase) activity using dinitrosalicylic acid (DNS).

The defined basal medium was based on Modified Davis minimal media; 7 g $K_2HPO_4$/liter, 3 g $KH_2PO_4$/liter, 1 g $(NH_4)_2SO_4$/liter, 0.5 g sodium citrate/liter, 0.1 g $MgSO_4 \cdot 7H_2O$/liter. The original recipe includes glucose. Glucose was not added, and the sugars listed below were individually added to result in 11 separate media.

TABLE 1

| Substrate | Enzyme Assays IU/mL | | | |
| --- | --- | --- | --- | --- |
|  | Xylanase | Pectinase | Amylase | CMCase |
| Glucose | 0 | 0 | 0.222 | 0.119 |
| Mannose | 0.185 | 0.251 | 0.275 | 0.457 |
| Xylose | 0.127 | 0.232 | 0.074 | 0.092 |

TABLE 1-continued

| Substrate | Enzyme Assays IU/mL | | | |
| --- | --- | --- | --- | --- |
|  | Xylanase | Pectinase | Amylase | CMCase |
| Arabinose | 0.125 | 0.225 | 0.094 | 0.15 |
| Cellulose | 0.327 | 0.178 | 0.073 | 0 |
| Pectin | 0.135 | 0 | 0.215 | 0.172 |
| Starch | 0 | 0.186 | 0 | 0 |
| Xylan | 0.378 | 0.057 | 0.09 | 0.119 |
| CMC | 0.168 | 0.206 | 0 | 0.081 |
| Pine acid hydrolysate | 0 | 0 | 0.093 | 0.093 |
| Pine acid hydrolysate, overlimed | 0.133 | 0 | 0.104 | 0.104 |

CMC refers to carboxymethylcellulose.

These data indicate that *P. amylolyticus* produces xylanase, pectinase, amylase, and cellulase when grown in the minimal basal media in the presence of various carbon sources.

EXAMPLE 2

Use of *P. amylolyticus* in fermentation process with yeast, where production of antimicrobial polymyxin E reduces bacterial contaminants and the production of enzymes degrades biomass.

*P. amylolyticus* is grown in spent (i.e., post fermentation) biomass to produce antimicrobials and enzymes that can then be fed into the beginning of the next round of the process. For instance, pine is pretreated using acid hydrolysis with an acid such as, for instance, an anhydride of an acid, such as an inorganic acid. Enzymes from a commercial supplier are added to start the digestion of the biomass to produce sugars such as glucose, mannose, xylose, etc. Examples of commercially available enzymes that can be added include Novozyme 13 (a mixture of cellulases, Novozymes, Franklinton, N.C.) and Cellobiase (Novozymes, Franklinton, N.C.). The yeast ferment the glucose and mannose to ethanol while the xylose, a carbohydrate that typically cannot be used by yeast, accumulates in the medium. *P. amylolyticus* is added to the fermenter after the ethanol is distilled. *P. amylolyticus* then use the xylose as a carbon source in order to grow and to produce enzymes. Salts and other components that result in a better environment for growth of *P. amylolyticus* may be added to the fermenter, such as the ingredients of the defined basal medium described above, but without any supplemental carbon source.

More pretreated pine is added to the fermenter, along with more yeast. Because of the production of enzymes by *P. amylolyticus*, the amount of commercial enzyme required to digest the biomass is lower. Consequently, the costs associated with fermentation are decreased. Further, since *P. amylolyticus* may produce polymyxins (DeCrescenzo Henriksen et al., Lett. Appl. Microbiol., 2007, 45:491-496), the possibility of contamination by prokaryotic microbes is decreased.

EXAMPLE 3

Production of *P. amylolyticus* that does not produce polymyxin E.

*P. amylolyticus* C27 was mutagenized with Tn917 (on plasmid pLTV3) as follows.

Electrocompetent cell preparation. *P. amylolyticus* C27 was streaked out on Brain Heart Infusion (BHI) agar and incubated overnight at 37° C. A single colony was used to inoculate 5 mL BHI broth, which was then incubated overnight at 37° C. with shaking. Fifty milliliters BHI broth was inoculated with 0.5 mL (1%) of C27 overnight culture and grown to $OD_{600}$ 0.2, at which time penicillin was added to a final concentration of 0.12 mg/L. The culture was then grown to $OD_{600}$ 0.8, harvested by centrifugation, washed three times in electroporation buffer (316 mM sucrose, 1 mM $MgCl_2$), and resuspended in 0.5 mL of the same buffer.

Plasmid preparation. Plasmid pLTV3, containing Tn917, (Camilli et al., J. Bacteriol., 1990, 172:3738-3744, available from the Bacillus Genetic Stock Center, The Ohio State University) was prepared from *Escherichia coil* K12 ER2925 using a Qiagen spin miniprep kit. The use of this *E. coli* strain provides plasmid DNA free of methylation.

Electroporation. Electrocompetent C27 cells were mixed with 0.5 ug pLTV3 plasmid DNA and electroporated in a 4 mm gap length cuvette (2.5 kV, 200Ω, 25 uF). After 1 hour recovery at 32° C., cells were plated on BHI containing erythromycin (ERM) at 5 mg/ml, and incubated at 32° C.

Library construction. *P. amylolyticus* C27 pLTV3 was streaked out on BHI-ERM and incubated at 32° C. for 48 hours. A single colony was used to inoculate 5 mL BHI-ERM broth which was incubated at 32° C. overnight with shaking. Fifty milliliters BHI-ERM broth was inoculated with 0.5 mL (1%) of C27 pLTV3 overnight culture and grown at 32° C. to $OD_{600}$ 0.2 at which time the temperature was increased to 41° C. and held for 5 hours. Cells were then plated on BHI-ERM agar and incubated at 37° C. for two days.

Library screening. Colonies from BHI-ERM plates at 37° C. were picked and patched into 200 uL BHI-ERM broth in 96-well plates. After two days of growth, a 96-pin replicator was used to transfer cells to BHI-ERM plates. These plates were grown for 48 hours at 37° C., and, at that time, a soft agar culture seeded with *E. coli* was poured onto the surface of the plates. After 24 hours of growth, colonies displaying no inhibition of *E. coli* were chosen for further study.

Four thousand colonies were screened and one antibiotic loss of function mutant was identified. This strain was designated *P. amylolyticus* 97-6. *E. coli* strains were capable of growth in culture extracts from this mutant.

EXAMPLE 5

Use of *P. amylolyticus* antibiotic production mutant strain in fermentation processes with bacteria, whereby production of enzymes degrades biomass.

*P. amylolyticus* strains that are incapable of producing polymyxin E can be used in conjunction with prokaryotic microbes, such as *E. coli*, that ferment biomass to yield ethanol. The *P. amylolyticus* mutant is grown in spent (i.e., post fermentation with a prokaryotic microbe) biomass to produce enzymes that can then be fed into the beginning of the next round of the process. For instance, pine is pretreated using acid hydrolysis with an acid such as, for instance, an anhydride of an acid, such as an inorganic acid. Enzymes from a commercial supplier are added to start the digestion of the biomass to produce sugars such as glucose, mannose, xylose, etc. The prokaryotic microbes ferment the glucose, mannose, and, typically, some xylose to ethanol. *P. amylolyticus* is added to the fermenter after the ethanol is distilled. *P. amylolyticus* then uses the remaining carbon sources to grow and to produce enzymes. Salts and other components that result in a better environment for growth of *P. amylolyticus* may be added to the fermenter, such as the ingredients of the defined basal medium described above. Supplemental carbon could be added if the fermenting prokaryotic microbe, such as *E. coli*, consumes all the carbon sources during the initial fermentation.

More pretreated pine is added to the fermenter, along with more *E. coli*. Because of the production of enzymes by *P. amylolyticus*, the amount of commercial enzyme required to digest the biomass is lower, which lowers the cost of producing ethanol from biomass. Furthermore, the commercial enzymes used are typically fungal, and often have optimal activities at temperatures that are lower than the temperatures used for fermentation by a prokaryotic microbe.

EXAMPLE 6

Fermentation of $SO_2$ Pretreated Southern Yellow Pine (10% solids) with Yeast or Both Yeast and *P. amylolyticus* Strain 27C64

Pretreated G3S2 pine was produced as follows. Loblolly pine from Georgia, USA, was chipped to a particle size of 10 mm or less. Chips were then pretreated with gaseous sulfur dioxide in two steps. A batch of a known amount of chips was treated with 2.5% $SO_2$ wt/wt of moisture content in chips, at a temperature of 190° C. for 5 minutes. Following this pretreatment step, the material was pressed using a hydraulic press to collect liquid. This liquid was called G3L1 and was not used in the experiments described herein. The pretreated solids (material remaining after the liquid was pressed out and removed), was then washed with water and pressed to a dry matter content of 40%. These washed dry matter solids are now called G3S1.

In the second step, G3S1 was impregnated with 2.5% $SO_2$ wt/wt of moisture content in the solids, and allowed to react at a temperature of 210° C. for 5 minutes. The samples obtained using these two steps of pretreatment were named G3L2 (L is for the liquid stream) and G3S2 (S is for the solids stream). Moisture content of the pretreated G3S2 pine was 71.53%.

Fermentation with Yeast: Experiments A and B

Two bioreactors each containing 20 g dry wt. (10% solids) of pretreated G3S2 pine were autoclaved at 121° C. and treated with Novozyme 13 (15 FPU/g) and Cellobiase (60 U/g) (Novozymes, Inc. Franklinton, N.C.). Active dried yeast (ADY, obtained from North American Bioproducts Corporation, Duluth, Ga.) was inoculated at a concentration of 2 g/l in each vessel. The total volume of fermentation was 200 ml. Sterile water was added to the bioreactor to mimic the addition of 27C64 to C and D below.

Fermentation with Yeast and C64: Experiments C and D

Two bioreactors each containing 20 g dry wt. (10% solids) of pretreated G3S2 pine were autoclaved at 121° C. and treated with Novozyme 13 (12 FPU/g) and Cellobiase (60 U/g). Active dried yeast was inoculated at a concentration of 2 g/l in each bioreactor. Five hundred milliliters of overnight grown culture of 27C64 was centrifuged, pellet resuspended in a small volume of 2×TSB and 5×10$^7$ cells (roughly 0.2 grams dry weight of bacteria) were added to the fermentor. The total volume of fermentation was 200 ml.

Table 2 Ethanol production from pretreated pine G3S2 at 10% solids with and without coinoculation with the bacterium 27C64. Columns A and B (experiments A and B) used only yeast cells and 15 FPU cellulase and 60 U cellobiase per gram dry weight of G3S2. Columns C and D (experiments C and D) used only 12 FPU cellulase and 60 U cellobiase per gram dry weight of G3S2 with inoculation of 27C64 cells at the same time as yeast and commercial enzyme addition.

| | Ethanol (g/L): | | | |
|---|---|---|---|---|
| | Yeast | | Yeast and 27C64 | |
| Time (h) | A | B | C | D |
| 24 | 22.71 | 23.08 | 23.56 | 23.33 |
| 48 | 26.40 | 26.84 | 30.07 | 28.99 |
| 144 | 27.21 | 28.37 | 30.28 | 29.93 |

Maximum ethanol per FPU of Novozyme enzyme in experiments A and B: Average of ethanol production was 27.79 g/L*0.2 L=5.558 g ethanol/300 total FPU=0.0185 g ethanol/FPU Novozyme cellulase enzyme. At 48 hours 26.62 g/L*0.2 L=5.324/300 FPU total=0.01775 g ethanol/FPU Novozyme cellulase enzyme.

Maximum ethanol per FPU of Novozyme enzyme in experiments C and D: Average of ethanol production was 30.105 g/L*0.2 L=6.021 g ethanol/240 total FPU=0.0251 g ethanol/FPU Novozyme cellulase enzyme. At 48 hours 29.53 g ethanol/L=5.906 g ethanol/240 FPU=0.0246 g ethanol/FPU Novozyme cellulase enzyme. The maximum ethanol concentration theoretically possible for this pretreated pine G3S2 was 31.8 g ethanol per liter of fermentation broth.

These data clearly demonstrate it was possible to reduce the concentration of Novozyme cellulase enzyme by 20%, from 15 FPU/g dry wt biomass to 12 FPU/g dry wt biomass without sacrificing ethanol production.

EXAMPLE 7

Fermentation of $SO_2$ Pretreated Southern Yellow Pine (15% solids) with a Culture of Yeast and *P. amylolyticus* Strain 27C64: Effect of Step Wise Addition of G3S2 Solids Pretreated G3S2 pine was produced as described in Example 6. Moisture content of pretreated G3S2 pine was 71.53%.

Experiment 1

Effect of Step Wise Addition of G3S2 Solids (Total Solids 15%) and Yeast

Ten percent dry weight G3S2 solids were fermented simultaneously with enzymes Novozyme 13 (15 FPU/g dry wt) and Cellobiase (60 U/g) and active dried yeast (2 g/l). Eight grams G3S2, enzymes Novozyme 13 and Cellobiase for 8 g solids, and 0.1 g ADY were added to the above bioreactors at 12 hours, 24 hours, and 36 hours. The total volume was approximately 250 ml after the solids additions.
Results.

TABLE 3

| | Ethanol (g/L): | |
|---|---|---|
| | G3S2 | |
| Time (h) | A | B |
| 0 | 0.67 | 0.56 |
| 12* | 14.04 | 13.10 |
| 24* | 27.97 | 27.86 |
| 36* | 32.30 | 32.78 |
| 48 | 40.35 | 40.35 |
| 72 | 42.92 | 42.26 |

TABLE 3-continued

| | Ethanol (g/L): | |
|---|---|---|
| | G3S2 | |
| Time (h) | A | B |
| 96 | 46.64 | 46.02 |
| 120 | 43.69 | 44.56 |

*Ethanol after addition of 8 g solids

These data demonstrate maximum ethanol production at 96 hours was 46.3 g/L*0.250 L=11.575 g ethanol when yeast was used.

Experiment 2

Effect of Step Wise Addition of G3S2 Solids (Total Solids 17.6%) with Yeast and C64

Pretreated G3S2 pine was produced as described in Example 6. Moisture content of pretreated GA3 pine was 71.53%.

I. Fermentation Using 27C64 Cells and Culture Broth Containing Enzymes Added 24 Hours Prior to Inoculation with Yeast.

A bioreactor containing 20 g dry wt. (10% solids) of pretreated G3S2 pine was autoclaved at 121° C. and treated with Novozyme 13 (12 FPU/g) and Cellobiase (60 U/g). 8×TSB (25 ml) was added as a nutrient source. Five hundred milliliters of 27C64 culture was centrifuged and 75 ml of supernatant was added to each of two bioreactors. At time −24 hours, 27C64 cell pellets were resuspended in TSB and added to the bioreactors. The fermenters were mixed well and a sample removed for plate counts. At time −24 hours, i.e., 24 hours before addition of yeast, approximately $2 \times 10^5$ cells per ml were present. ADY was inoculated at a concentration of 2 g/l in the bioreactor at time zero.

Eight grams dry weight G3S2 solids, enzymes Novozyme 13 and Cellobiase for 8 g solids, and 0.1 g ADY were added to the above bioreactors at 36 hours, 48 hours, and 60 hours. The total volume was approximately 290 ml. At 24 hours the number of C64 cells had decreased to $1 \times 10^5$ cells per ml.

II. Fermentation Using Yeast, 27C64 Cells, and Culture Broth Containing Enzymes Added at the Same Time as the Yeast Inoculum.

A bioreactor containing 20 g dry wt. (10% solids) of pretreated G3S2 pine was autoclaved at 121° C. and treated with Novozyme 13 (12 FPU/g) and Cellobiase (60 U/g). 8×TSB (25 ml) was added as a nutrient source. Two hundred fifty milliliters of 27C64 culture was centrifuged and 75 ml supernatant containing 27C64 enzymes was added to the bioreactor. The cell pellet was resuspended in a small amount of TSB, added to the bioreactor, and mixed well. Samples were removed for plate counts and reflected approximately $3 \times 10^5$ cells per ml were present at time zero. At time zero, 27C64 pellets which were resuspended in TSB were inoculated along with ADY at a concentration of 2 g/l.

Eight grams dry weight G3 S2 solids, enzymes Novozyme 13 and Cellobiase for 8 g solids, and 0.1 g ADY were added to the above bioreactors at 12 hours, 24 hours, and 36 hours. The total volume was approximately 290 ml. At 24 hours the number of C64 cells had decreased to $7 \times 10^4$ cells per ml.

Spore count at time 0 and 24 hours: no spores detected.

TABLE 4

| | Ethanol (g/L): | |
|---|---|---|
| Time (hours) | 27C64 cells and broth alone, yeast addition at time zero (24 hours after addition of 27C64 cells) | 27C64 cells, broth, and yeast added all at time 0. |
| −24 | 0 | NA |
| 0 | 1.30 | 1.00 |
| 12* | 14.70 | 15.31 |
| 24* | 25.51 | 24.48 |
| 36* | 31.21 | 30.77 |
| 48 | 42.78 | 35.24 |
| 72 | 45.08 | 40.15 |
| 96 | 46.60 | 46.12 |
| 120 | 48.00 | 47.00 |
| 144 | 48.05 | 48.15 |

−24 refers to 24 hours prior to inoculation with yeast.
*Ethanol after addition of 8 g solids At 96 hours the average ethanol production was 46.12 g/L*0.29 L=13.38 g ethanol for 0.0253 g ethanol/FPU Novozyme cellulase. The average maximum ethanol (144 hours) was 48.15 g/L*0.290 L=13.96 g ethanol for 0.0264 g ethanol/FPU Novozyme cellulase.

In summary, fermentations with addition of *P. amylolyticus* 27C64 cells at the same time as inoculation with yeast reached the same or greater ethanol concentrations with 20% less commercial enzyme. Adding 27C64 cells and broth containing *Paenibacillus* enzymes 24 hours prior to yeast inoculation changes the overall process time by 24 hours without increasing ethanol yield. The ethanol concentrations for 48 and 72 hours after yeast inoculation, with and without pre-incubation with 27C64, were higher for the fermentations with pre-incubations, however by 96 hours there was no difference in ethanol yields (see Table 5).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

TABLE 5

Comparison of ethanol production with and without *Paenibacillus* cells, with and without solids addition.

| Parameter | 27C64 cells added. | FPU Commercial Enzyme added. | Solids added after fermentation began. | Final solids % dry wt | Time (hours) | Ethanol (g/L) | Total Ethanol (g) | grams Ethanol/FPU Novozyme Cellulase |
|---|---|---|---|---|---|---|---|---|
| 10% Solids | No | 15 FPU | No | 10% | 48 | 26.62 | 5.324 | 0.0178 |
| | | | | | 144 | 27.79 | 5.558 | 0.0185 |
| | Yes | 12 FPU | No | 10% | 48 | 29.53 | 5.906 | 0.0246 |
| | | | | | 144 | 30.11 | 6.021 | 0.0251 |
| 10% Solids | No | ??? | Yes | 15% | 48 | 40.35 | 10.09 | 0.0153 |
| | | | | | 96 | 46.33 | 11.58 | 0.0175 |
| | | | | | 120 | 44.11 | 11.03 | 0.0167 |
| | Yes, added with supernatant and yeast at t = 0. | 12 FPU | Yes | 15% | 48 | 35.24 | 10.26 | 0.0194 |
| | | | | | 96 | 46.12 | 13.38 | 0.0253 |
| | | | | | 144 | 48.15 | 13.96 | 0.0264 |
| | Yes, added with supernatant 24 hours prior to addition of yeast | 12 FPU | Yes | 15% | 48 | 42.78 | 12.41 | 0.0235 |
| | | | | | 96 | 46.60 | 13.07 | 0.0248 |
| | | | | | 144 | 48.05 | 13.93 | 0.0264 |

* Time is equal to the hours after yeast were added to the fermenters.

What is claimed is:

1. A method of producing polymyxin comprising:
providing a composition comprising spent hydrolysates;
culturing a *Paenibacillus* spp. in the composition under conditions suitable for the production by the *Paenibacillus* spp. of an enzyme having saccharifying activity, wherein the saccharifying activity is selected from xylanase activity, pectinase activity, amylase activity, mannanase activity, and cellulase activity, wherein polymyxin is produced.

2. The method of claim 1 wherein the spent hydrolysates are obtained from fermentation of a pretreated lignocellulosic material.

3. The method of claim 1 wherein the culturing results in a second composition comprising the *Paenibacillis* spp. and an enzyme having saccharifying activity, the method further comprising mixing the second composition with a composition comprising a pretreated lignocellulosic material to result in a fermentation composition.

4. The method of claim 3 further comprising contacting the fermentation composition with an enthanologenic yeast.

5. The method of claim 3 wherein the yeast is *Saccharomyces cerevisiae*.

6. A method of producing polymyxin comprising:
culturing a *Paenibacillus* spp. in a composition comprising spent hydrolysates under conditions suitable for the production by the *Paenibacillus* spp. of an enzyme having saccharifying activity, wherein the enzyme is selected from a xylanase, a pectinase, an amylase, a mannanase, and a cellulase, wherein the culturing results in a second composition comprising the *Paenibacillis* spp. and an enzyme having the saccharifying activity, wherein polymyxin is produced.

7. The method of claim 6 further comprising substantially removing the *Paenibacillis* spp. from the second composition.

8. The method of claim 6 wherein the *Paenibacillis* spp. is *P. amylolyticus*.

9. The method of claim 1 wherein the *Paenibacillus* spp. is *Paenibacillus amylolyticus*.

10. The method of claim 1 wherein the *Paenibacillis* spp. produces an enzyme having saccharifying activity when incubated on a medium comprising inorganic salts and a carbon source selected from glucose, mannose, xylose, arabinose, cellulose, pectin, starch, xylan, carboxymethylcellulose, or a combination thereof.

11. The method of claim 4 wherein the ethanologenic microbe is a yeast.

12. The method of claim 6 wherein the spent hydrolysates are obtained from fermentation of a pretreated lignocellulosic material.

* * * * *